United States Patent [19]
Brierley

[11] Patent Number: 5,965,889
[45] Date of Patent: Oct. 12, 1999

[54] IMAGING STAGE FOR FOURIER TRANSFORM INFRARED SPECTROMETER

[75] Inventor: Philip R. Brierley, Madison, Wis.

[73] Assignee: Pike Technologies of Wisconsin, Inc., Madison, Wis.

[21] Appl. No.: 08/964,508

[22] Filed: Nov. 5, 1997

[51] Int. Cl.[6] ........................... G01N 21/01
[52] U.S. Cl. .................. 250/339.11; 250/339.12; 250/341.8
[58] Field of Search ............ 250/339.11, 339.12, 250/341.8

[56] References Cited

U.S. PATENT DOCUMENTS

| | | | |
|---|---|---|---|
| 4,730,882 | 3/1988 | Messerschmidt | 350/96.1 |
| 5,106,196 | 4/1992 | Brierley | 356/445 |
| 5,172,182 | 12/1992 | Sting et al. | 356/244 |
| 5,210,418 | 5/1993 | Harrick et al. | 250/339 |

OTHER PUBLICATIONS

Minano, Juan, et al., A high–gain, compact, nonimaging concentrator: RXI, Applied Optics, Dec. 1, 1995.
The Split Pea Accessory, Harrick, Starna.
Thunderdome, Spectra–Tech, Inc., Shelton, CT.
Single Bound HATR Accessory, Spectra–Tech Product Data Sheet, PD–22, Jan. 1996.
Developments and Modifications of the Basic Parabolic Concentrator, Chapter 5.
Golden Gate Single Reflection Diamond ATR.

Primary Examiner—Robert H. Kim
Assistant Examiner—Andrew H. Lee
Attorney, Agent, or Firm—Quarles & Brady LLP

[57] ABSTRACT

An internal reflection element for a Fourier transform infrared spectrometer employs a single lens providing refraction and internal reflection of an infrared beam so as to focus the beam on a centrally located sample surface and to collect and focus radiation reflected from this sample surface for analysis.

8 Claims, 2 Drawing Sheets

IMAGING STAGE FOR FOURIER TRANSFORM INFRARED SPECTROMETER

STATEMENT REGARDING FEDERALLY SPONSORED RESEARCH OR DEVELOPMENT

CROSS-REFERENCE TO RELATED APPLICATIONS

BACKGROUND OF THE INVENTION

The present invention relates to Fourier transform infrared spectrometer's (FTIR spectrometers) and, in particular, to a stage for use with such a spectrometer for making attenuated total reflectance (ATR) measurements.

Fourier transform infrared spectroscopy is a technique for studying the composition of matter by measuring the characteristic absorption of specific wave lengths of infrared radiation. The sample may be measured either with transmitted or reflected radiation.

In transmission spectroscopy, a beam of infrared radiation of known and time variant spectral composition is passed through a transmissive sample. The resulting transmission absorption spectrum is then compared to standard transmission absorption spectra to identify spectral absorption characteristics of the sample permitting identification of the sample's constituents.

With opaque samples, the technique of specular reflection spectroscopy may be used. In reflection spectroscopy, the beam of infrared radiation is directed against the surface of a sample at a predetermined angle of incidence. The spectrum of the energy reflected at an opposing reflection angle is then measured. As with transmission spectroscopy, the resulting reflection absorption spectrum may be compared to known reflection absorption spectra to reveal information about the composition of the sample or the coating of the surface of the sample. One type of specular reflection measurement is termed attenuated total reflectance (ATR) spectroscopy.

Making ATR measurements of a material involves placing the material against the sample surface of an infrared transmitting crystal. Infrared light is introduced into the crystal and made to internally reflect off the sample surface. During this reflection, the sample may absorb some of the energy of the infrared beam which interacts with the sample. A successful measurement requires that the sample be in intimate contact with the crystal since this interaction with the infrared beam only occurs over a few microns from the surface of the crystal. These crystals are sometimes referred to as internal reflection elements (IRE).

IREs that allow for a single internal reflection are called single-bounce IREs. Single-bounce IREs may come in a variety of shapes including trapezoidal shape prisms, cylindrical rods or hemispherical domes. They offer the advantages of requiring only a small sample and of needing only low clamping forces to hold the sample against the sample surface. The drawback to single-bounce IREs is that there is only one interaction between the sample and crystal and the resulting spectrum may be weak.

In order to increase the light energy coupled to the sample, multi-bounce IREs may be used. In multi-bounce IREs, multiple reflections occur against the side of the crystal contacting the sample to increase the amount of attenuation and improve the obtained spectra. Unfortunately, such multi-bounce crystals require that the sample be held in close proximity to the crystal over a relatively broad area increasing the total force which must be applied to the sample.

Single and multi-bounce crystals are typically limited to having a single transmissive element so as to reduce Fresnel reflection losses occurring when light passes into or out of a transmissive element. One problem with both types of crystals is that not all the light passing through the IRE strikes the sample surface. The light that does not strike the sample surface is commonly termed stray light and may distort the spectral features that are being investigated.

BRIEF SUMMARY OF THE INVENTION

The present invention provides the benefits of a single bounce IRE (e.g., small sample size and low clamping force) together with the high sensitivity normally associated with a multi-bounce IRE. A single lens element, using refraction and internal reflections, focuses an image of the infrared source on the sample surface and re-focuses the image of the reflected light on the spectrometer detector, increasing the proportion of the infrared energy interacting with the sample and ultimately used to form the infrared spectrum.

Specifically, the present invention provides a stage for a Fourier transform infrared spectrometer, the spectrometer having a source of infrared radiation and a radiation detector. The stage includes a lens element having opposed first and second surfaces converging at the edges of the lens wherein a first portion of the first surface is shaped to refract and focus a beam of infrared radiation from the source passing through the first portion of the first surface into the lens so as to direct the beam through the lens to a first portion of the second surface. The first portion of the second surface is shaped to reflect and focus the beam in the lens to a second portion of the first surface which in turn is shaped to internally reflect and focus the beam in the lens to a sample area against which a sample may be placed at the center of the lens on the second surface. The sample area is shaped to reflect the beam in the lens to a third portion of the first surface which is shaped, in turn, to internally reflect and focus the beam in the lens to a second portion of the second surface which then reflects and focuses the beam in the lens to a fourth portion of the first surface where it is refracted and focused in passing through the fourth portion out of the lens to be received by the radiation receiver.

It is one object of the invention to provide a compact single element focusing IRE. By employing both refraction and internal reflection of the converging surfaces of the lens element, infrared energy may be focused on the sample area.

The first and second portions of the second surface may be coated with a reflecting material.

Thus, it is another object of the invention to provide a compact and easily manufactured single element IRE. Coating surfaces of the IRE with a reflective material allow beam paths to be employed which would otherwise not be internally reflecting.

The lens may have an outwardly extending plateau at its center and the sample area may be on this plateau.

The first and second portions of the second surface may be encased in a protective mount with the sample area protruding through an opening in the protective mount.

Thus, it is another object of the invention to provide a robust stage for a spectroscopy machine which protects the IRE.

The sampling area may be greater in area than a 500 micron diametered circle.

Thus, it is another object of the invention to provide a stage providing substantially more sampling area than present single bounce systems.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

DETAILED DESCRIPTION OF THE INVENTION

Figure 1:
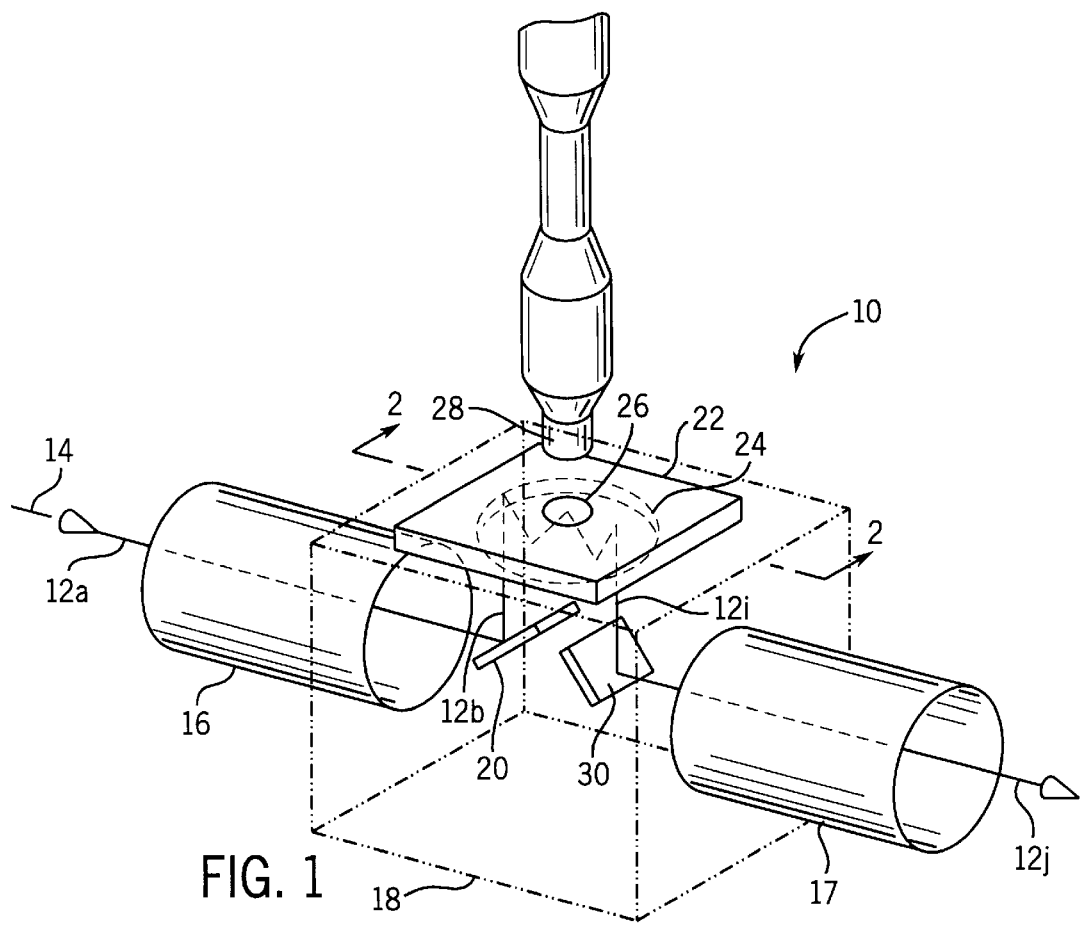
FIG. 1 is a perspective view, in partial phantom, of an FTIR spectrometer stage of the present invention showing the optical path from the spectrometer source through the IRE element of the present invention and back to the spectrometer detector.

Referring to FIG. 1, a stage 10 for an FTIR spectrometer is positioned to receive an infrared beam 12a modulated according to well-known FTIR techniques. The beam 12a is received along a principal axis 14 through a first tubular shroud 16 to the body 18 of the stage 10.

Figure 2:
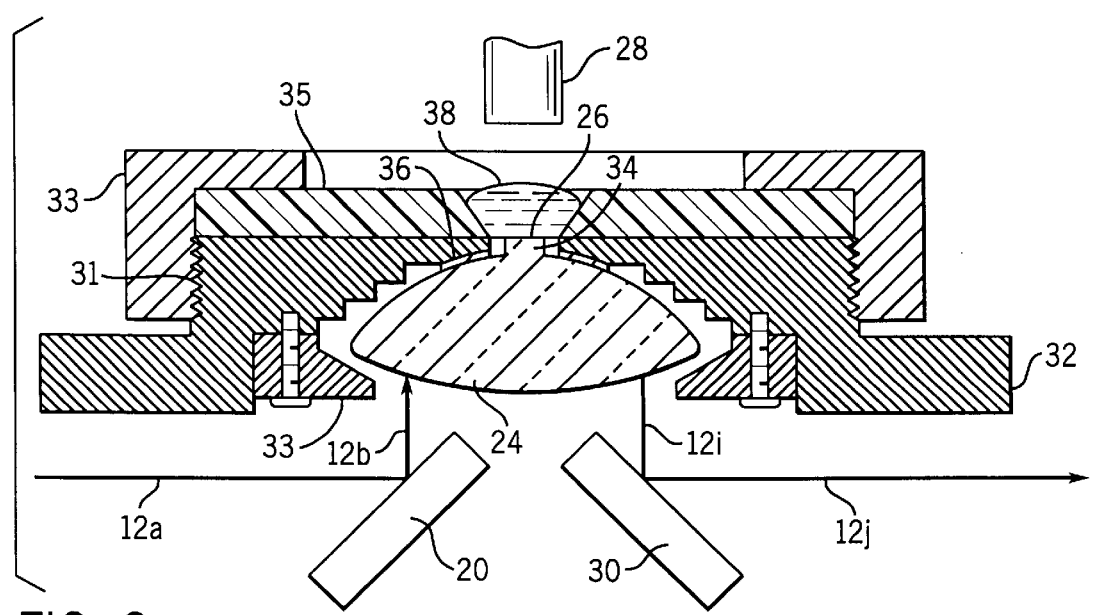
FIG. 2 is a fragmentary cross section taken along line 2—2 of FIG. 1 showing a first embodiment of the IRE element of the present invention inserted into the optical path of the spectrometer with a liquid well adapter in place for measuring liquids holding a material to be sampled against the sample surface.

A front surface mirror 20 canted at 45° with respect to axis 14 reflects infrared beam 12a upward as infrared beam 12b toward IRE assembly 22 holding internal reflectance element (IRE) 24. The IRE 24 receives the infrared beam 12b and, as will be described, focuses it on a sample surface 26 being a generally horizontal circular area. Referring momentarily to FIG. 2, sample surface 26 is positioned beneath a micrometer anvil 28 such as may be used to compress a sample 38 downward against the sample surface 26 in the case of solid samples.

Referring again to FIG. 1, light reflected internally off the sample surface 26 is returned into the body 18 of the stage 10 as downward traveling infrared beam 12i. There it is directed, by a second front surface mirror 30 angled at 45° with respect to axis 14, as horizontally traveling infrared beam 12j through second tubular shroud 17 generally aligned with axis 14 and infrared beam 12a.

Referring now to FIG. 2, the IRE assembly 22 includes a metallic stage block 32 having a generally horizontal planar upper surface with a central aperture through which the sample surface 26 of the IRE 24 may extend. The stage block 32 may have upwardly extending threads 31 about its periphery mating with a retaining ring 33 that may hold a well adapter 35 against the upper surface of the stage block 32. The well adapter 35 may have a central conical aperture aligned with the sample surface 26 to hold samples 38 that are liquid. A diamond protective plate may be applied to sample surface 26 to protect it from abrasion from the sample 38. The sample surface 26 is the upper portion of a plateau 34 extending upward from the generally disk shaped IRE 24 and is sealed within the aperture in the IRE assembly 22 by an indium gasket 36 and without the use of O rings, glue or epoxy resins. The indium material flows into the gaps between the materials providing a sealing of small gaps and accommodating thermal expansion as well as providing good support for the IRE 24. The IRE 24 is held within a cavity against the indium gasket 36 by means of a retaining ring 33.

Figure 3:
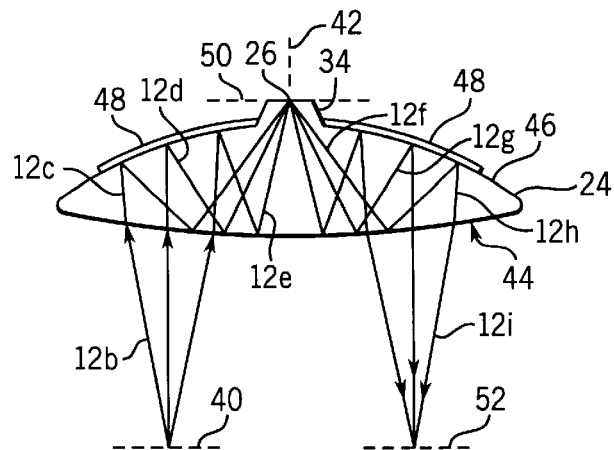
FIG. 3 is a simplified depiction of the IRE element of FIG. 2 removed from the protective stage assembly showing light ray paths from a first focal plane to the sample surface and back to a second focal plane.

Referring now to FIG. 3, IRE 24 will receive light from a focused image of the infrared source at image plane 40 positioned beneath a left side of the IRE 24. This light is focused again at the sample surface 26 and reflected light from the sample surface 26 is focused again at image plane 52 positioned beneath a right side of the IRE 24. The image at image plane 52 will be refocussed as an image on the FTIR detector (not shown).

The IRE 24 is radially symmetric about an axis 42 perpendicular to axis 14 and in a first embodiment has a convex front surface 44 and a convex rear surface 46 with plateau 34 centered along axis 42 and perpendicular thereto. Rays 12b passing from each point in image plane 40 are received over a first area of the front surface 44 and refracted to form beams 12c passing through the IRE 24 and directed toward rear surface 46. The material of the IRE 24 is transparent to infrared radiation and conducts the beams 12c to a first portion of the rear surface 46 to the left of plateau 34 coated with a thin layer of aluminum 48.

The rear surface 46 outside of plateau 34 is generally convex so as to reflect infrared beam 12c as beams 12d in focused fashion toward the front surface 44 at an angle of incidence sufficient to provide for complete internal reflection of beams 12d (as beams 12e) by a second portion of front surface 44 to the left of axis 42.

The curvature of the surfaces through which beams 12b pass, and beam 12c and 12d are reflected, are such as to bring the beams 12 into focus again at a sample image plane 50 aligned with sample surface 26. Thus, the IRE 24 presents a large entrance aperture to beams 12b from image plane 40 and focuses substantially all the energy from image plane 40 on sample surface 26.

Sampling surface 26 is normal to axis 42 and beams 12e are a sufficient angle so as to reflect internally off of sample surface 26 as beams 12f. Sampling surface 26 is not coated with aluminum.

The reflected beams 12f are symmetric with respect to beams 12e, and in striking a third portion of the front surface 44 are internally reflected as beams 12g in much the same manner as beams 12d are reflected as beams 12e, however, the third portion of the front surface 44 is to the right of the axis 42.

Beams 12g pass through the material of the IRE 24 to strike a second portion of rear surface 46 of IRE 24 to the right of axis 42. This second portion is also coated with aluminum 48 so that beams 12g are fully reflected downward again as beams 12h to a fourth portion of front surface 44 to the right of axis 42 where they pass out of the IRE 24 and are refracted as beams 12i.

The curvature of the front surface 44 and rear surface 46 are such as to again cause beams 12i to form an image at image plane 52 corresponding to the images at the image planes 50 and 40.

By providing the appropriate curvatures of the surfaces 44 and 46, the IRE 24 may be imaging, that is may bring about a focusing of the beams at planes 40, 50 and 52 thus maximizing the amount of energy interacting with the sample 38 (shown in FIG. 2) and minimizing the amount of light transmitted through the IRE 24 that does not interact with the sample 38. The IRE 24 is preferably constructed of an optically transparent material such as zinc selenide (ZnSe) germanium or amorphous transmitting infrared glass (AMTIR), the latter being a special glass commercially available from Amorphous Materials of Garland, Tex.

Other materials which may be used for the IRE include, but are not limited to, arsenic modified selenium glass (SeAs), cadmium sulphide (Cds), cadmium telluride (CdTe), cesium iodide (CsI), diamond (C), germanium (Ge), indium antimonide (InSb), silicon (Si), saphire ($Al_2O_3$), silver bromide (AgBr), silver chloride (AgCl), sulfur (S), sulphur selenium glasses (SxSey), thallium bromide (TlBr), thallium chloride (TlCl), KRS5 ((TlBr-TlCl), zinc sulphide (ZnS) and zirconia ($ZrO_2$, cubic).

Depending on the material used for the IRE 24, a variety of shapes of surfaces 44 and 46 may be used. Generally, surfaces 44 and 46 will be converging and in the preferred embodiment are spherical ellipsoidal surfaces. The exact surfaces may be determined for a given material and application through the use of commercially available ray tracing programs as will be understood to those of ordinary skill in the art.

Figure 5:
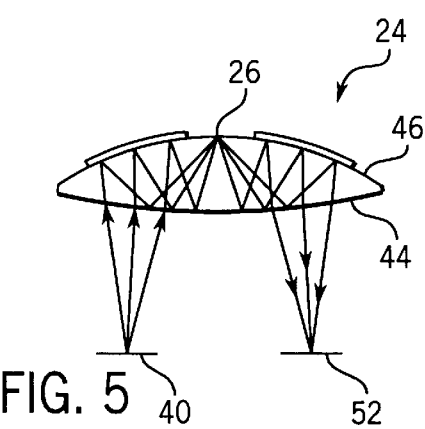

Referring now to FIG. 5, the plateau 34 may be eliminated with a slight adjustment of the surfaces 44 and 46 to provide a smoothly continuous surface 46 with the sample surface 26 flush with the remainder of the rear surface 46 and having the same curvature.

Figure 4:
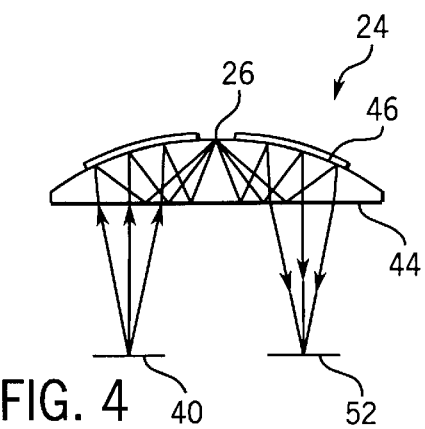
FIGS. 4 through 8 are alternative embodiments of the IRE of FIG. 3.
Figure 6:
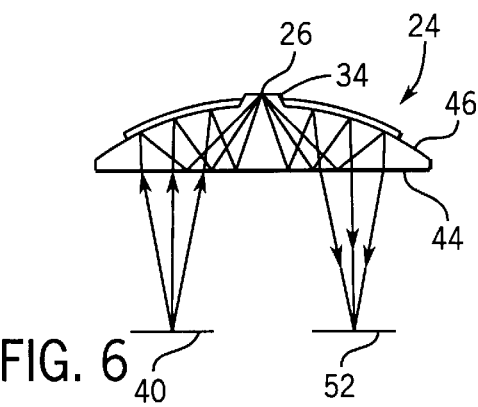
Figure 7:
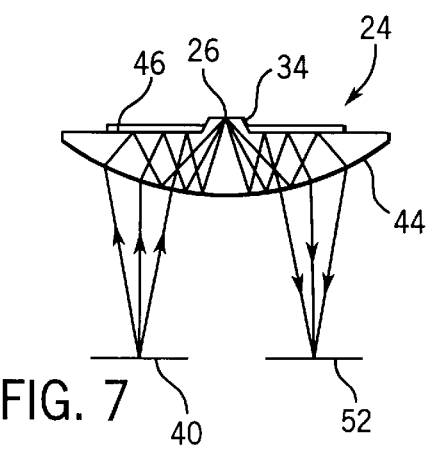
Figure 8:
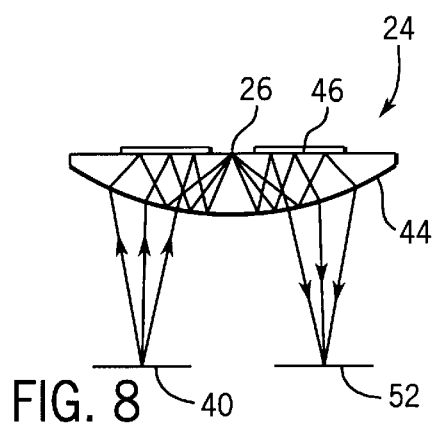

Referring to FIGS. 4, 6, 7 and 8, the bi-convex design of the IRE 24 of FIG. 3 may be replaced with a plano convex design with or without the plateau 34. Thus, the rear surface 46 may be convex and the front surface 44 may be planar as shown in FIGS. 4 and 6 or the front surface 44 may be convex and the rear surface 46 may be planar as shown in FIGS. 7 and 8. In each of these embodiments, refraction and internal reflection are still used to focus a beam from a first image plane 40 onto the sample surface 26 and again onto a second image plane 52 outside of the IRE 24.

The above description has been that of a preferred embodiment of the present invention. It will occur to those that practice the art that many modifications may be made without departing from the spirit and scope of the invention. In order to apprise the public of the various embodiments that may fall within the scope of the invention, the following claims are made.

I claim:

1. A stage for a Fourier transform infrared spectrometer, the spectrometer having a source of infrared radiation and a radiation detector, the stage comprising:
    a lens element having opposed first and second surfaces, the surfaces converging at edges of the lens, wherein:
        (i) a first portion of the first surface is shaped to refract a beam of infrared radiation from the source passing through the first portion of the first surface into the lens so as to direct the beam through the lens to a first portion of the second surface;
        (ii) the first portion of the second surface is shaped to reflect the beam through the lens to a second portion of the first surface;
        (iii) the second portion of the first surface is shaped to reflect the beam through the lens to a sample area against which a sample may be placed near the center of the lens on the second surface;
        (iv) the sample area is shaped to reflect the beam through the lens to a third portion of the first surface;
        (v) the third portion of the first surface is shaped to reflect the beam through the lens to a second portion of the second surface;
        (vi) the second portion of the second surface is shaped to reflect the beam through the lens to a fourth portion of the first surface; and
        (vii) the fourth portion of the first surface is shaped to refract the beam passing through the fourth portion out of the lens to the radiation receiver.

2. The stage of claim 1 wherein the first and second portions of the second surface are coated with a reflecting material.

3. The stage of claim 1 wherein the lens has an outwardly extending plateau at its center and wherein the sample area is on the plateau.

4. The stage of claim 3 wherein the lens has the first and second portions of the second surface encased in a protective material with the sample area protruding through an opening in the protective material.

5. The stage of claim 1 wherein the one of the first and second surfaces, excluding only a region of the sampling area, is flat.

6. The stage of claim 3 where the sampling area is flat.

7. The stage of claim 1 where the sampling area is curved and greater in area than a 500 micron diametered circle.

8. The stage of claim 1 where the sampling area is flat.

* * * * *